[19] United States Patent
Delle-Vedove et al.

[11] Patent Number: 4,537,201
[45] Date of Patent: Aug. 27, 1985

[54] PROCESS AND DEVICE FOR DETECTING THE RESPONSE OF THE HEART TO AN ELECTRICAL STIMULATION PULSE

[75] Inventors: Daniel Delle-Vedove, Aulnay sur Mauldre; Yves Lallemand, Vernon; Olivier Hubert, Paris, all of France

[73] Assignee: Societe Europeenne de Propulsion, Puteaux, France

[21] Appl. No.: 530,522

[22] Filed: Sep. 9, 1983

[30] Foreign Application Priority Data

Sep. 23, 1982 [FR] France ................................ 82 16034

[51] Int. Cl.³ .......................... A61B 5/02; A61N 1/36
[52] U.S. Cl. .............................. 128/697; 128/419 PG; 128/708
[58] Field of Search ................. 128/419 PG, 696-701, 128/708, 731, 733, 741

[56] References Cited

U.S. PATENT DOCUMENTS 3,495,077  2/1970  Hiltz et al. .......................... 128/731
3,699,947  10/1972  Maynard .............................. 128/731
3,878,833  4/1975  Arneson et al. ...................... 128/708
4,114,627  9/1978  Lewyn et al. ................. 128/419 PG

FOREIGN PATENT DOCUMENTS 0017848 10/1980 European Pat. Off. .

Primary Examiner—William E. Kamm
Assistant Examiner—Mitchell J. Shein
Attorney, Agent, or Firm—Shenier & O'Connor

[57] ABSTRACT

The present invention relates to a process and device for detecting the response of the heart to an electrical stimulation pulse, comprising: collecting, after the end of the stimulation pulse, a first signal v which represents the electrode potential in open circuit and of which the variation in time t, from an original instant $t_o$ is of substantially logarithmic form:

$$v = v_o + k \text{Log} \frac{t}{t_o},$$

$v_o$ being the value of v at instant $t_o$ and k being a parameter connected in particular with the duration and amplitude of the stimulation pulse, converting the first signal v into a second signal of which the variation in time is substantially linear and, detecting in said second signal a non-linear component representing the signal produced by the provoked contraction of the heart.

13 Claims, 5 Drawing Figures

PROCESS AND DEVICE FOR DETECTING THE RESPONSE OF THE HEART TO AN ELECTRICAL STIMULATION PULSE

The present invention relates to the detection of the response of the heart to an electrical stimulation pulse.

The domain of application of the invention is that of pacemakers, particularly of implantable cardiac stimulators of all types.

A pacemaker consists in a generator of electrical stimulation pulses connected to an electrode placed in contact with the excitable tissues of the cardiac muscle. Contraction of the heart takes place when the electrical energy delivered to the electrode exceeds a certain threshold (stimulation threshold) which is capable of varying in the course of time. The same electrode is generally also used for detecting the natural contractions of the heart in order to inhibit the operation of the stimulator when the heart beats naturally above a certain rhythm.

It would also be desirable to detect the provoked contractions, i.e. those produced in response to a stimulation pulse in order, in particular, to adapt the energy furnished by the stimulator to the real needs of the heart and thereby to reduce the consumption of electrical energy. However, such detection is rendered very difficult as the passage of the stimulation current provokes an electrical polarization of the electrode/heart interface, i.e. an accumulation of ions on the surface of the electrode equivalent to the charge of a capacitor. The disappearance of this charge after the passage of the stimulation current (depolarization) is more or less rapid depending on the intensity of the inverse current succeeding the stimulation current but its duration is such (for example of the order of 200,ms) that the depolarization voltage possesses, at the moment of the provoked contraction, an amplitude of several hundreds of mV much greater than the potential variation (some mV) produced by the contraction. Consequently, the response of the heart to the stimulation pulse is "masked" by the depolarization of the electrode.

To detect this response without being hindered by the depolarization voltage, it has been proposed to use at least one detection electrode different from the stimulation electrode. The obvious drawback of this solution lies in the necessity of the permanent presence of a plurality of electrodes.

It has also been proposed to apply the stimulation pulse and to detect the contraction provoked, by using the same electrode and by combatting depolarization of this electrode.

For example, FR Pat. No. 2 241 287 and EP No. 0057944 propose applying to the electrode a current of sign opposite that of the stimulation current. The duration of depolarization is certainly thus reduced for the residual depolarization voltage, at the moment of the provoked contraction, to be sufficiently low so as not to mask the response of the heart. However, the application of a current opposite the stimulation current may give rise to a phenomenon of electrolysis with passage of metal ions in the heart and possible corrosion of the electrode. In FR No. 2 374 023, it is also proposed to accelerate depolarization by passage of an inverse current, the electrode voltage being measured with a view to detection when the variation of voltage, at the end of depolarization, is slow. However, this latter device uses measuring circuits which require adjustment as a function of the nature of the electrode used.

It is an object of the present invention to allow detection of provoked contraction, without additional electrode and without the drawbacks of the known devices which combat depolarization of the electrode.

This object is attained thanks to a process of detection comprising the steps, according to the invention, of:

collecting, after the end of the stimulation pulse, a first signal v which represents the electrode potential in open circuit and of which the variation in time t, from an original instant $t_o$ is of substantially logarithmic form:

$$v = v_o + k.\text{Log}\frac{t}{t_o},$$

$v_o$ being the value of v at instant $t_o$ and k being a parameter connected in particular with the duration and amplitude of the stimulation pulse, converting the first signal v into a second signal of which the variation in time is substantially linear and, detecting in said second signal a non-linear component representing the signal produced by the provoked contraction of the heart.

The invention is based on the observation that the natural depolarization voltage (i.e. in open circuit) of the electrode varies in time in substantially logarithmic manner whatever the nature of the electrode used. Linearization of the signal representing the electrode voltage in open circuit then allows easy detection of the signal produced by the provoked contraction of the heart.

According to a first embodiment of the invention, this linearization comprises a phase of transformation by a function f of exponential type: $f(x)=Ae^{Kx}$, A and K being two parameters. To obtain a second linear signal, either the signal v must be attenuated by a factor $\alpha$ such that $\alpha kK=1$—with the result that f(v) is proportional to $$e^{\alpha kK}\text{Log}\frac{t}{t_o},$$

i.e. to t—or the value of K must be adjusted so that $kK=1$.

According to a second embodiment of the invention, linearization comprises a phase of generation of a reference signal $v_{ref}$ varying in logarithmic fashion such that $$v_{ref} = v'_o + K'\text{Log}\frac{t}{t_o}, v'_o$$

being the value of $v_{ref}$ at instant $t_o$ and K' being a parameter, and a phase of comparison of the first signal v with the reference signal. To obtain a second linear signal, either signal v must be attenuated by a factor $\alpha'$ such that $\alpha'k=K'$, or the value of K' must be adjusted so that $K'=k$.

For detecting, in the second signal, a linear component representing the desired information, filtering is effected with a view to extracting this component and the filtered magnitude is compared with a predetermined threshold value.

It is also an object of the invention to provide a device for carrying out the process defined hereinabove.

This object is attained thanks to a device which comprises:

a controlled switch adapted to place the electrode in open circuit in response to the reception of a control signal, and a detection circuit comprising an input circuit connected to the electrode to collect a first signal v which represents the electrode potential; a converter circuit receiving said first signal and furnishing on its output a second signal varying in time in substantially linear manner when it receives a signal varying in time in substantially logarithmic fashion; and a detector receiving said second signal and adapted to detect therein a non-linear component representing the signal produced by the provoked contraction of the heart.

The invention will be more readily understood on reading the following description with reference to the accompanying drawings, in which.

Figure 1:
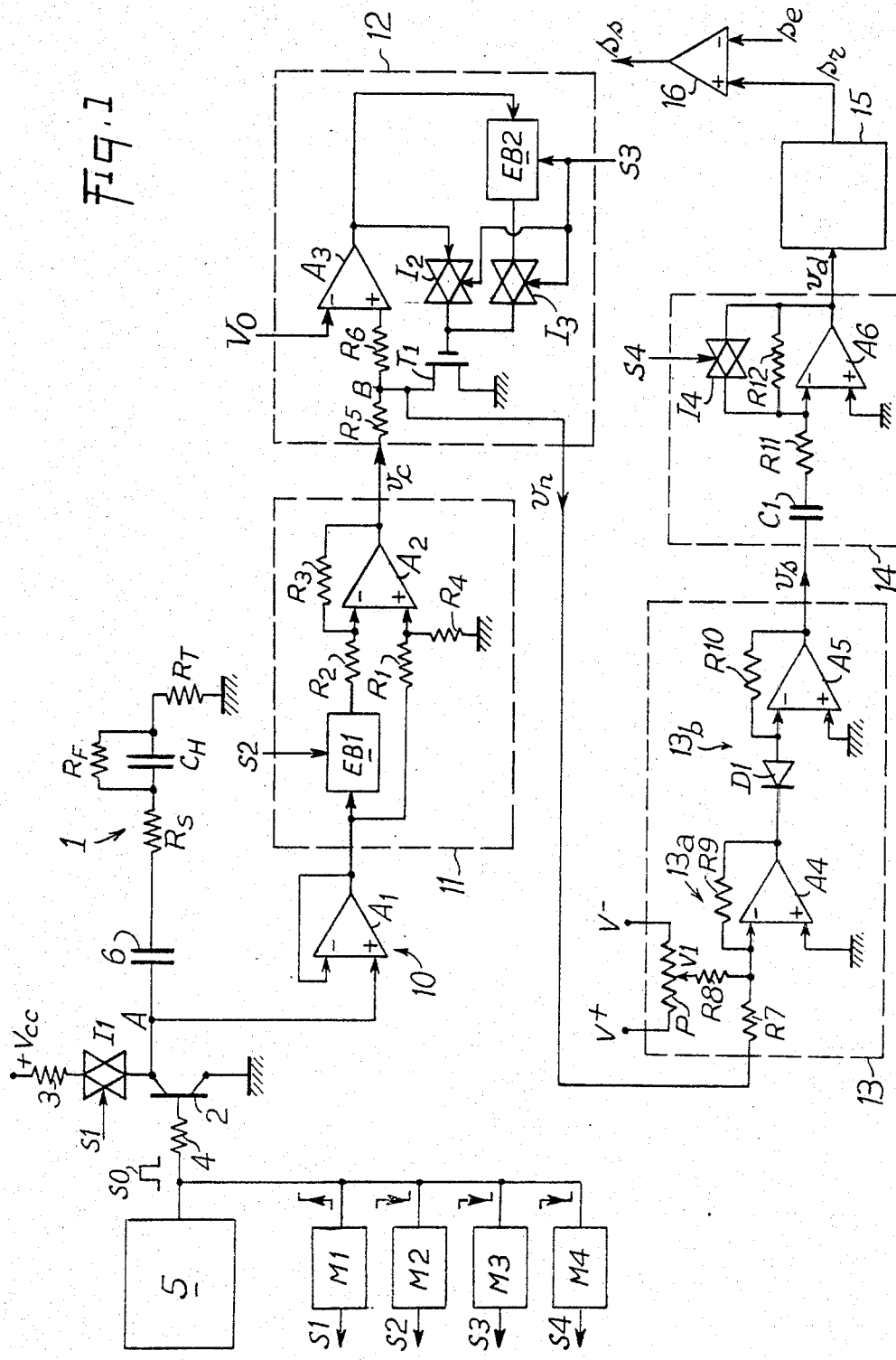
FIG. 1 is a diagram of an embodiment of a detection device according to the invention.

Referring now to the drawings, FIG. 1 shows at 1 the equivalent diagram of a stimulation electrode or probe in contact with a patient's heart. The series resistor $R_S$ represents the resistance of the probe wire. The parallel circuit formed by the capacitor $C_H$ and the resistor $R_F$ represents the interface between the probe and the heart and is in series between $R_S$ and the resistor $R_T$ of the heart tissues. The collector of a transistor 2 is connected by a resistor 3 to a terminal taken to a positive potential $V_{cc}$ and its emitter is connected to a terminal taken to a reference potential (ground). The base of transistor 2 is connected by a resistor 4 to the output of a control circuit 5. A capacitor 6 is connected between the collector of the transistor 2 and the electrode 1. The elements which have just been described are the usual components of a conventional cardiac stimulator, or pacemaker. When the transistor 2 is non-conducting, capacitor 6 is charged at voltage $V_{cc}$. A stimulation pulse SO produced by the control circuit (line a of FIG. 2) renders transistor 2 conducting; capacitor 6 discharges partially in the heart, this constituting the negative stimulation pulse.

According to the invention, a switch I1 is connected between the terminal at potential $V_{cc}$ and point A common to the collector of transistor 2 and to capacitor 6. The switch I1 is a switch of analog type (for example a transistor) whose opening is controlled by a signal S1 (line b of FIG. 2). This signal S1 is a pulse produced at instant $t_o'$ in response to the rising edge of SO by a monostable multivibrator M1 connected to the output of the control circuit 5. The duration T1 of S1 is chosen so as to cover production by the heart of the signal resulting from the provoked contraction in response to SO. By way of indication, T1 is included between 100 and 200 ms. At the end of time T1, the switch I1 closes, which allows capacitor 6 to recharge through resistor 3. The latter is chosen to be sufficiently low for capacitor 6 to be recharged before the end of the refractory period, i.e. the lapse of time following a pulse (provoked or natural) during which the natural QRS signal detector is inhibited in order not to be disturbed by the T wave. In fact, as already indicated, a conventional pacemaker is usually provided with a natural QRS detector which blocks the generation of electrical stimulation pulses when the heart beats naturally above a certain rhythm. The refractory period is generally of the order of 300 ms.

The detection circuit according to the invention is connected to point A and comprises an input circuit 10, formed by an amplifier A1 with high input impedance, a zero phasing circuit 11, a scaling circuit 12, an amplifier 13 of "antilogarithmic" type, a derivative circuit 14 and a filter 15.

Figure 2:
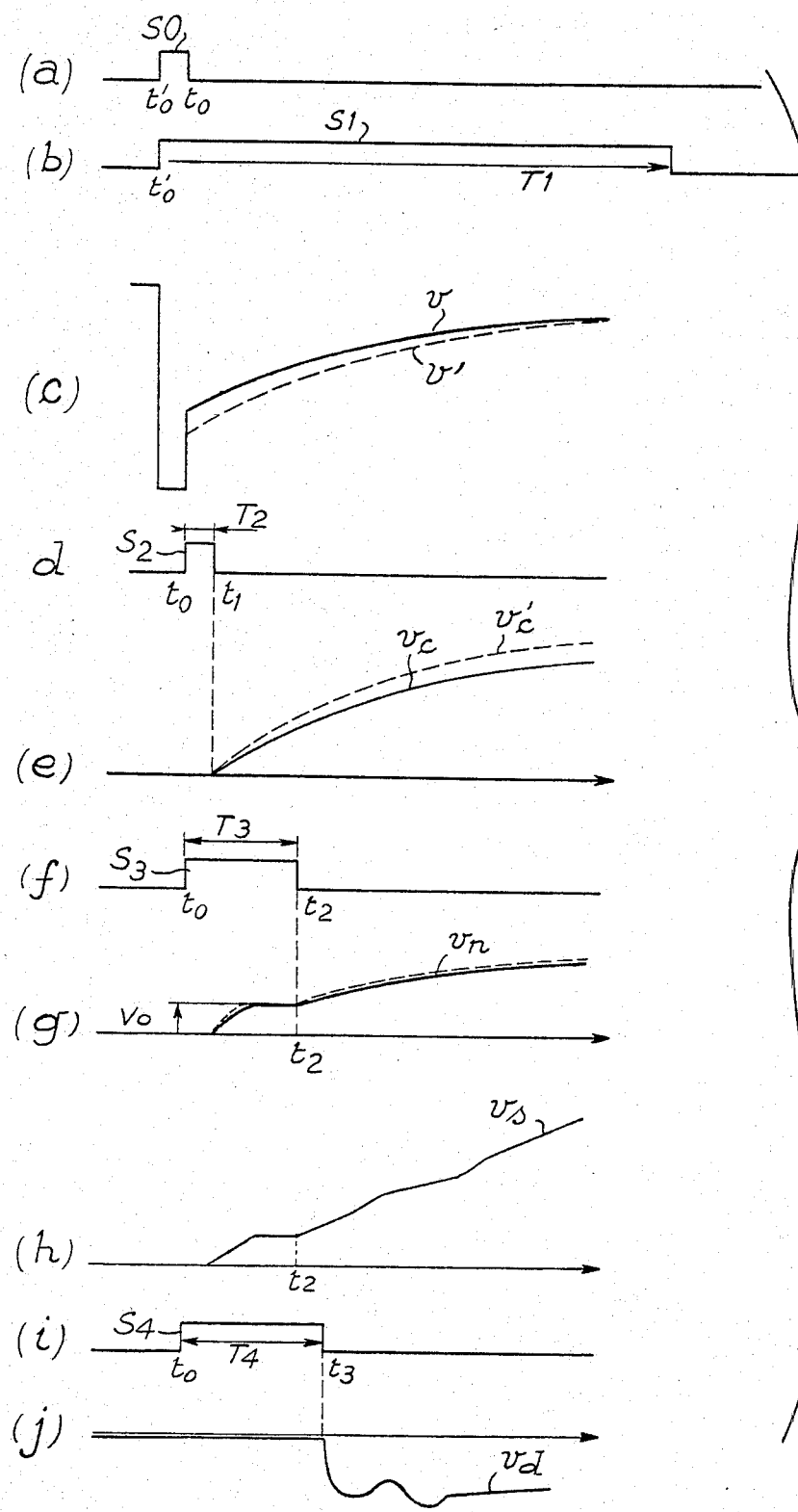
FIGS. 2 to 4 illustrate the wave forms of signals at different points of the device of FIG. 1.

The switch I1 being open, the signal v taken at point A and copied in the input stage 10 has the form illustrated in line c of FIG. 2. For the duration of SO, for example of the order of 1 ms, (instant $t'_o$ to instant $t_o$), the stimulation pulse IS is applied to the heart. At instant $t_o$, transistor 2 becomes non-conducting. As the switch I1 is open, the voltage v then represents the electrode voltage in open circuit. From instant $t_o$, depolarization of the electrode is translated by a rise of the voltage v and the present invention is based on the observation that the variation of v as a function of time t is of substantially logarithmic form:

$$v = v_o + k \, \text{Log} \, \frac{t}{t_o}, \, v_o$$

being the value of v at instant $t_o$ and k a coefficient. It has been checked that the variation of the potential of depolarization is of logarithmic form whatever the probe used and the type of stimulator. A linearization of v then allows an easier detection of the response of the heart. However, the values of $v_o$ and of k vary according to the types of electrode and the operational conditions, particularly depending on the duration and amplitude of the stimulation pulse. Thus, with the same stimulator, the rise of the electrode voltage may be of the form $$v' = v'_o + k' \, \text{Log} \, \frac{t}{t_o},$$

$v'_o$ being different from $v_o$ and k' being different from k (cf. dashed line in line c of FIG. 2). Before the phase of linearization, v is therefore successively standardized by zero phasing and scaling.

Zero phasing consists in imposing a zero value on the voltage v at a predetermined instant $t_1$ following instant $t_o$. To this end, the signal v coming from the input circuit A1 and received by zero phasing circuit 11 is applied on the one hand to a sample-and-hold circuit EB1 and, on the other hand, via a resistor R1, to the non-inverter input of a differential amplifier A2. The inverter input of the amplifier A2 receives, via a resistor R2, the output signal of EB1. The output of A1 is connected to the inverter input by a resistor R3 whilst the non-inverter input of A1 is connected to ground by a resistor R4. The sample-and-hold circuit EB1 is controlled by a signal S2 (line d of FIG. 2) in the form of a pulse produced in response to the falling edge of SO by a multivibrator M2 connected to the output of the control circuit 5. The duration T2 of the pulse S2 is such that, from instant $t_1$ (falling edge of S2), EB1 is controlled to latch its output signal at the value v at instant $t_1$. By way of indication, $T_2 = 1$ ms. At the output of circuit 11, a voltage of the form $$v_c = k \text{ Log} \frac{t}{t_o + T_2}$$

is therefore obtained (line e of FIG. 2). The curve representative of $v_c$ depends on the value of k (cf. curve $v'_c$ in dashed lines corresponding to v').

Scaling is effected by means of the attenuator circuit 12. A voltage divider formed by a resistor R5 in series with the drain/source path of a field effect transistor T1 is connected between the input of the circuit 12 receiving $v_o$ and ground. The common point B between R5 and T1 forms the output of circuit 12 on which the scaled signal $v_n$ (line g of FIG. 2) is delivered. Point B is connected by a resistor R6 to the non-inverter input of an operational amplifier A3 used as a comparator and of which the inverter input is connected to a terminal taken to an adjustable, predetermined reference potential $V_o$. The output of A3 is connected to the control electrode (grid) of transistor T1 via, on the one hand, a controlled switch I2 and, on the other hand, the series circuit formed by a sample-and-hold circuit EB2 and a controlled switch I3. Switches I2 and I3 are switches of static type controlled by a signal S3 (line f of FIG. 2) in the form of a pulse produced in response to the falling edge of SO by a monostable multivibrator M3 connected to the output of the control circuit 5. The duration T3 of the pulse S3 is greater than T2, for example of the order of 5 ms. Switches I2 and I3 are controlled in synchronism so that one is open whilst the other is closed, and vice versa. For the duration of S3 (instant $t_0$ to instant $t_2$), I2 is closed and I3 is open. At the end of S3, I2 opens and I3 closes. The pulse S3 also controls the sample-and-hold circuit EB2 to hold the output signal of the latter at the value acquired at instant $t_2$. The attenuator operates as follows: When the voltage $v_n$ reaches value $V_0$, the comparator A3 delivers a signal which, applied to the grid of T1, controls the drain/source resistance of this transistor so that $v_n$ is maintained at value $V_0$. At time $t_2$, the output voltage of A3 is copied by the sample-and-hold circuit EB2. I2 is open, whilst I3 is closed to maintain the grid of T1 at the voltage copied by EB2. The drain/source resistance of T1 then remains constant. A coefficient of attenuation $\alpha$ is applied, via circuit 12, to the voltage $v_c$, such that, at instant $t_2$, the voltage $v_n$ is equal to $V_0$. $v_n$ then equals $$\alpha \, k \text{ Log} \frac{t}{t_o + T_2} \text{ with } \alpha = V_o/k \text{ Log} \frac{t}{t_o + T_2}.$$

From instant $t_2$, the curve of variation of $v_n$ is the same whatever the values of $v_o$ and k.

The standardized voltage $v_n$ is applied to the input of an antilogarithmic amplifier circuit 13, i.e. an exponential gain circuit. The circuit 13 comprises an input stage 13a forming gain adjustment circuit and an antilogarithmic amplifier 13b proper. The input stage 13a comprises an operational amplifier A4 on the inverter input of which is applied the sum of $v_n$ and of an adjustable voltage $V_1$. To this end, the output of circuit 12 is connected to the inverter input of A4 by a resistor R7 whilst the slider of a potentiometer P is connected to this same inverter input by a resistor R8. The ends of the potentiometer P are connected to two terminals taken to fixed potentials, positive V+ and negative V−, respectively. A resistor R9 connects the output of A4 to its inverter input whilst the non-inverter input of A4 is connected to ground. The antilogarithmic amplifier 13b comprises, in manner known per se, a non-linear element formed by a diode D1 of which a terminal is connected to a first input (inverter input) of an operational amplifier A5 of which the other input is connected to ground. A resistor R10 connects the output of A5 of its inverter input. The other terminal of D1 is connected to the output of A4. The circuit 13b produces on its output a voltage: $v_s = a.e^{k \, v_e}$, a and k being constants and ve being the voltage applied to the input of 13b. From time $t_2$, $v_2$ therefore equals a.e $k(V1+v_n)$ or $v_s = ae^{kV_1} e^{\alpha kK}$ Log $t_2/t_o+T_2$. Thus, if $\alpha kK=1$, $v_s$ is, beyond $t_2$, a substantially linear function of time t: $v_s=K_1 t$ (line h of FIG. 2). Equality $\alpha kK=1$ is obtained by adjusting the value $V_o$, whilst the slope $K_1$ of $v_s$ is adjustable by adjusting the gain of the circuit 13 by adjusting the value $V_1$ by means of potentiometer P. The response of the heart (QRS wave) to the stimulation pulse is then translated by a non-linearity of $v_s$. Whilst this response is not discernible in the curve representative of v, it is, on the contrary, perfectly visible after the phase of linearization.

In order to accentuate the signal representing the response of the heart, the voltage $v_s$ is derived by means of the derivative circuit 14 connected to the output of the amplifier 13b. This derivative circuit comprises a series circuit formed by a capacitor C1 and a resistor R11 and connected between the output of A5 and the inverter input of an operational amplifier A6. The non-inverter input of the latter is connected to ground whilst its output is connected by resistor R12 to the inverter input. A switch 14 is connected in parallel on resistor R12. This switch is of static type controlled by a pulse S4 (line i of FIG. 2) produced in response to the falling edge of SO by a monostable multivibrator M4 connected to the output of the control circuit 5. The pulse S4 has a duration T4 greater than duration T3 of pulse S3. Switch I4 is maintained closed for the duration of S4, i.e. up to an instant $t_3$ delayed with respect to $t_2$, in order to avoid a saturation of the derivative circuit at moment $t_2$ of the change of slope of the output voltage of the antilogarithmic amplifier. The signal $v_d$ at the output of the derivative circuit 14 (line j of FIG. 2) is, from instant $t_4$, thus in the form of a D.C. voltage on which is superposed a non-continuous signal $s_r$ representing the response of the heart.

Filter 15 is a high pass filter enabling the signal $s_r$ to be extracted from the continuous component of $v_d$. At the output of filter 15, the signal $s_r$ is easily identifiable. To detect it, it suffices for example to apply the output signal of filter 15 to an input of a comparator 16 which receives on its other input a reference signal of adjustable threshold $s_e$. The comparator 16 furnishes an output signal $s_s$ when the instantaneous value of $s_r$ exceeds the threshold value $s_e$, thus translating the presence of a response signal of the heart to a provoked contraction.

Figure 3:
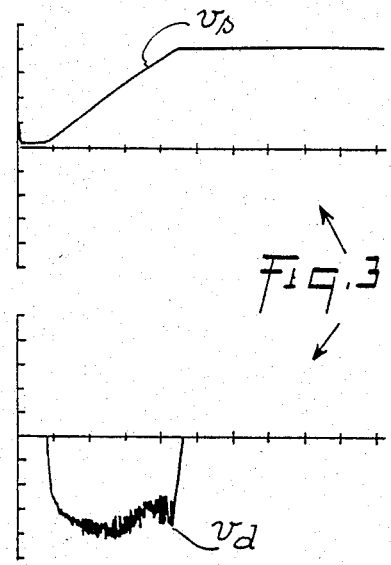
Figure 4:
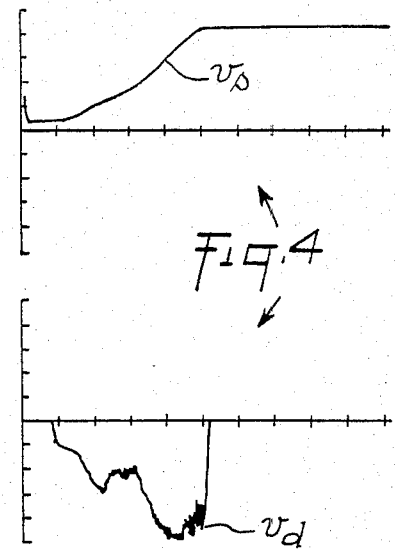

Tests have been carried out in the course of an operation for implanting a pacemaker on a patient. FIG. 3 illustrates the signals $v_s$, $v_d$ respectively at the output of the antilogarithmic amplifier, and at the output of the derivative circuit in the event of absence of response of the heart, whilst FIG. 4 illustrates these same signals in the event of presence of response of the heart. Despite the unfavourable conditions of recording in the operating theatre, FIGS. 3 and 4 demonstrate that the detection of the response of the heart is rendered possible without any difficulty or ambiguity thanks to the present invention.

Detection of such a response signal (electrostimulated QRS) may be used for adjusting, as known per se, the energy furnished by each stimulation pulse. For example, this energy is decreased by an increment when the electrostimulated QRS is detected, up to the absence of detection, the energy then being increased by several increments at once. Statistics relative to the numbers of natural QRS and electrostimulated QRS may also be established.

Figure 5:
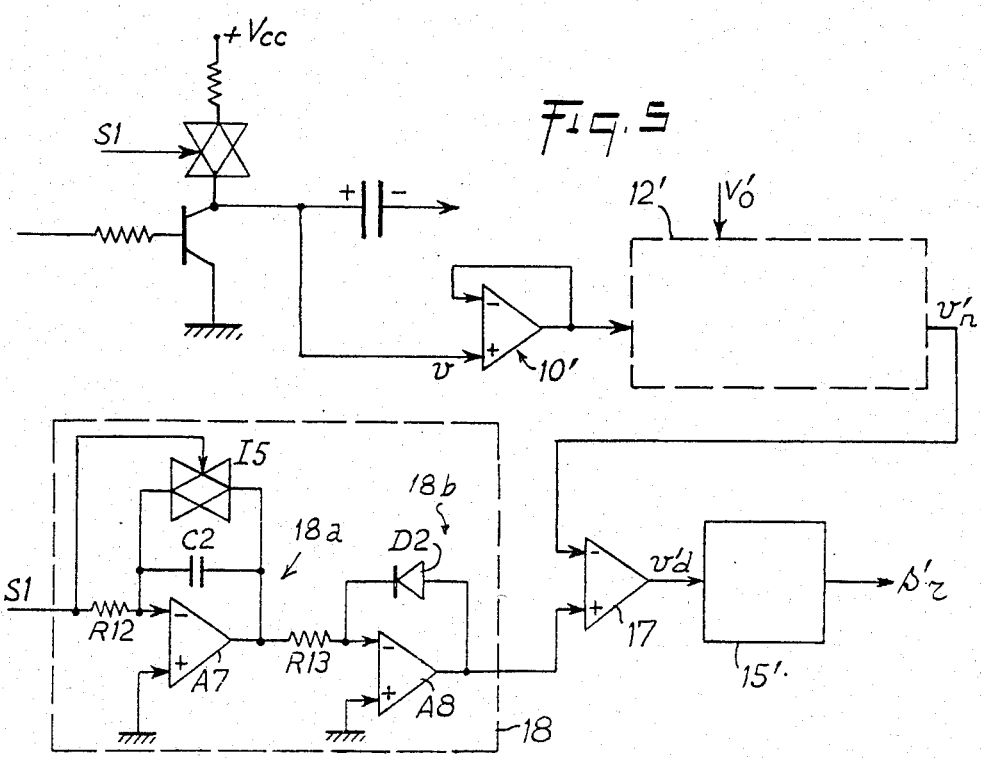
FIG. 5 is a diagram of another embodiment of a detection device according to the invention.

A variant embodiment of a detection device according to the invention is shown very schematically in FIG. 5.

The voltage v copied by the input circuit 10' similar to circuit 10 is applied to the input of a scaling circuit 12' similar to circuit 12. At the output of circuit 12', there is a voltage $v'_n$ which varies in logarithmic fashion $$v'_n = v_o + \alpha\, k\, \text{Log}\, \frac{t}{t_o}.$$

An operational amplifier 17, forming subtractor, receives the voltage $v'_n$ on a first input (inverter input) and receives on its second input a voltage w furnished by a logarithmic function generator 18. The voltage w varies in logarithmic manner as a function of time:

$$w = w_o + K'\text{Log}\, \frac{t}{t_o},$$

$w_o$ being the value of w at instant $t_o$. Operation of the generator 18 is for example controlled by the pulse S1. At the output of comparator 17, there is therefore a voltage $$v'_d = w_o - v_o + (K' - \alpha\, k)\text{Log}\, \frac{t}{t_o}.$$

The value of $\alpha$ is adjusted by adjusting the reference voltage $V'_o$ applied to the circuit 12' so that $K'=\alpha k$. A continuous level $v'_d$ similar to $v_d$ is thus obtained, this continuous level being filtered by a filter 15' to extract the non-continuous component $s'_r$.

Generator 18 comprises a stage 18a generating a saw-tooth voltage and a stage 18b converting this saw-tooth voltage into a signal varying according to a logarithmic function. Stage 18a comprises an amplifier A7 which receives the signal S1 on its inverter input via a resistor R12 and whose non-inverter input is connected to ground. A capacitor C2 is connected between the output of the amplifier A7 and its inverter input, in parallel with a static switch I5 whose opening is controlled by the pulse S1. Stage 18b is a conventional logarithmic amplifier circuit with an amplifier A8 whose inverter input receives the output signal of stage 18a via a resistor R13, whose non-inverter input is connected to ground and whose output is connected to the inverter input by a diode D2. As soon as the switch I5 is open, the voltage at the output of stage 18a decreases substantially linearly to return suddenly to its initial level at the moment of closure of I5 (end of S1). For the duration of S1, the signal varying linearly at the input of stage 18b is converted, at the output of the latter, into a signal w which increases in time in logarithmic manner.

In the foregoing, the conditions $\alpha kK=1$ and $\alpha k=K'$ are produced by adjusting the coefficient of attenuation $\alpha$. In a variant, it is not excluded to dispense with the scaling circuit and to adjust the gain K or the coefficient K' as a function of k, so that $kK=1$ or $K'=k$. In this case, the value of k may be obtained by measuring the variation of v for a determined interval of time $\Delta t$.

What is claimed is:

1. Process for detecting the response of the heart to an electrical stimulation pulse applied to an electrode in contact with the heart, by detection in a signal representing the potential of said electrode of a component produced by the provoked contraction of the heart, comprising the following steps of:

collecting, after the end of the stimulation pulse, a first signal v which represents the electrode potential in open circuit and of which the variation in time t, from an original instant $t_o$ is of substantially logarithmic form:

$$v = v_o + k\,\text{Log}\,\frac{t}{t_o},$$

$v_o$ being the value of v at instant $t_o$ and k being a parameter connected in particular with the duration and amplitude of the stimulation pulse, converting the first signal v into a second signal of which the variation in time is substantially linear and, detecting in said second signal a non-linear component representing the signal produced by the provoked contraction of the heart.

2. The process of claim 1, wherein the conversion of the first signal comprises a phase of transformation by a function f of exponential type $f(x)=Ae^{Kx}$, A and K being two parameters.

3. The process of claim 2, wherein said conversion also comprises a phase of attenuation of the first signal by a coefficient $\alpha$ such that $\alpha kK=1$.

4. The process of claim 2, wherein said conversion also comprises a phase of adjustment of the parameter K so that $K=k$.

5. The process of claim 1, wherein the conversion of the first signal comprises a phase of generation of a reference signal $v_{ref}$ varying in logarithmic fashion such that $$v_{ref} = v'_o + K'\text{Log}\,\frac{t}{t_o},\; v'_o$$

being the value of $v_{ref}$ at instant $t_o$ and K' being a parameter, and a phase of comparison of the first signal v with the reference signal.

6. The process of claim 5, wherein said conversion also comprises a phase of attenuation of the first signal by a coefficient $\alpha'$ such that $\alpha'k=K'$.

7. The process of claim 6, wherein said conversion also comprises a phase of adjustment of parameter K' such that $K'=k$.

8. Device for detecting the response of the heart to an electrical stimulation pulse applied to an electrode in contact with the heart, by detection, in a signal representing the potential of said electrode, of a component produced by the provoked contraction of the heart, said device comprising:

a terminal for connection to an electrode to be placed in contact with the heart;

means for generating stimulation pulses;

a controlled switch connected between said generating means and said terminal for placing said electrode in open circuit in response to the reception of a control signal; and a detection circuit comprising an input circuit connected to said terminal for receiving a first signal representative of the electrode potential, said first signal varying in time substantially in logarithmic manner when said electrode is placed in open circuit after the end of a stimulation pulse, linearization means connected to said input circuit for receiving said first signal and converting said first signal into a second signal varying in time substantially in linear manner, and detecting means connected to said linerarization means and receiving said second signal for detecting therein a non-linear component representing the signal produced by a contraction of the heart responsive to a stimulation pulse.

9. The device of claim 8, wherein said linearization means comprises a standardization circuit connected to said input circuit for receiving said first signal and delivering a standardized signal, and a conversion circuit having an exponential transfer function and connected to said standardization circuit for receiving said standardized signal and converting same to said second signal.

10. The device of claim 8, wherein said detection means comprises a derivative circuit receiving said second signal and a filtering circuit connected to said derivative circuit for extracting said non-linear component from the derivative of said second signal.

11. The device of claim 8, wherein said linearization means comprises a standardization circuit connected to said input circuit for receiving said first signal and delivering a standardized signal, a reference signal generator for generating a signal of which the variation in time is logarithmic and a substractor connected to said standardization circuit and reference signal generator for receiving said standardized signal and said reference signal and delivering said second signal representative of the difference between the standardized and reference signals.

12. The device of claim 9 wherein said standardization circuit comprises an attenuator circuit with controlled gain.

13. The device of claim 11, wherein said standardization circuit comprises an attenuator circuit with controlled gain.

* * * * *